United States Patent [19]

Wilson

[11] 4,055,478
[45] Oct. 25, 1977

[54] COULOMETRIC TITRATOR

[75] Inventor: Homer M. Wilson, Houston, Tex.

[73] Assignee: Petrolite Corporation, St. Louis, Mo.

[21] Appl. No.: 643,064

[22] Filed: Dec. 22, 1975

[51] Int. Cl.$^2$ ............................................. G01N 27/44
[52] U.S. Cl. ........................... 204/195 T; 204/195 M; 204/1 T
[58] Field of Search ........................... 204/1 M, 195 T

[56] References Cited

U.S. PATENT DOCUMENTS

| | | | |
|---|---|---|---|
| 3,275,533 | 9/1966 | Boronkay | 204/195 T |
| 3,398,064 | 8/1968 | Prost | 204/1 M |
| 3,441,490 | 4/1969 | Johansson | 204/195 T |
| 3,647,668 | 3/1972 | Linblad et al. | 204/195 T |
| 3,655,526 | 4/1972 | Christian | 204/195 T |

*Primary Examiner*—T. Tung
*Attorney, Agent, or Firm*—Sidney B. Ring; Hyman F. Glass

[57] ABSTRACT

A coulometric titrator for determining, at high accuracy and without time delay problems, small amounts of a specific (chloride) ion in a solution by the addition of a reactive ion. A sensor provides a first voltage representing the logarithm of the specific ion concentration to a differential amplifier which also receives as an input a signal from a reference electrode. The differential amplifier produces an error signal applied to a comparator and referenced therein to a certain reference voltage representing a desirable range of rates of change of the error output voltage. The comparator provides a sensor signal voltage representing the difference between the error signal and reference voltage. This sensor signal voltage is applied to an antilogarithm converter which produces an output signal that is proportional to the antilogarithm of the sensor signal voltage. The output signal is received by a reactive ion (silver metal) source means associated with a current source passing a unidirectional current flow between an inert cathode immersed in the solution and the reactive ion source means as an anode for the introduction of the reactive ion (silver) into the solution. As a result, the second signal voltage changes at a constant rate with time, and the reactive ion addition changes in a logarithmically decreasing amount with time in the sample solution until the stoichiometric end point is approached.

6 Claims, 4 Drawing Figures

COULOMETRIC TITRATOR

BACKGROUND OF THE INVENTION

1. Field of the Invention

This invention relates to the field of the electrochemistry, and more particularly, it relates to the coulometric analysis of specific ions in an electrolytic solution.

2. Description of the Prior Art

Coulometric analysis for specific ions in an electrolytic solution is a well known and established technique in the field of electrochemistry. The development of automatic functioning coulometric titrators for carrying out these analyses has produced many devices of which examples may be found in U.S. Pat. Nos. 3,275,533, 3,398,064, 3,441,490, and 3,647,668. Known automatic titration devices in the electrochemical field for conducting coulometric analysis depend upon a feedback loop which supplies an error signal establishing some fixed relationship between the addition of the reactive ion and a reference point at which the titration of the specific ion sought is believed to have been completed. Obviously, the feedback loop principle is a time domain function and suffers from compound errors. The electrodes employed in conducting the electrochemical analysis have an appreciable capacitance characteristic. Also, an appreciable time delay is caused by the diffusion of ions in the cell and principally the reactive ions introduced into the solution by the coulometric flow of current into the cell. Thus, the time delay problems make inaccurate and difficult-to-produce results in the coulometric titration of specific ions in an aqueous solution. The operator or an automatic feature must terminate with high accuracy and precision in electrochemical analysis the introduction of the reactive ion so that the ions may properly diffuse and the cell "coast" to what is believed to be the actual endpoint. The time delay problem varies with ion concentration and kind which also compounds the problem. The actual endpoint also changes not only with different types of ion but with different solvent composition.

It will be apparent that the coulometric titration employs sensors for the detection of the specific ion whose output, according to the Nernst equation, is a voltage proportional to the logarithm of the specific ion concentration. Thus, the most important component of the coulometric titration system is the sensor for the specific ion. The sensor has to indicate when a sufficient amount of the reactive ion has been added to completely convert this specific ion being analyzed for into a product effectively combining the specific and reactive ions into an insoluble or otherwise non-reactive salt. The sensor must be sensitive only to the specific ion being analyzed, and also, the reactive ion must combine only with the specific ion subject to analysis. Further, there must be a definite relationship in the chemical reaction between the specific and reactive ions and freedom from any interferences by extraneous ions with the desired reaction.

Obviously, automatic functioning coulometric titrators usually depend on electrochemical sensors whose voltage output is proportional to the logarithm of the concentration of the specific ion subject to analysis. This relationship is well known as the Nernst equation. This equation is a proper definition for the steady state of a solution or one where the ion concentrations are changing at a very slow rate. Mathematically, the equation defines that a certain percentage change in specific ion concentration will cause an incremental change in sensor output voltage that is the same independent of the actual magnitude of the specific ion concentration. Therefore, in the automatic coulometric titrator, the electrochemical sensor can be incorporated in its function as a percentage change indicator relative to the specific ion concentration.

As will be apparent, the addition of the reactive ion to the test solution at a constant rate produces ambiguities in the sensor's logarithmic voltage output. More particularly, the specific ion sensor changes voltage at the most rapid rate when the specific ion concentration is at equivalence since the largest percent change in specific ion concentration occurs at this point of the analysis. Therefore, the maximum sensor voltage change and the maximum rate of percentage change of specific ion concentration is known as the inflection point of the electrochemical analysis. High accuracy can be obtained with a constant rate of reactive ion addition only if the electrochemical analysis is done at very low rates of reactive ion addition so that the dynamic problems relating to the phenomena do not cause large analysis errors, but the time of analysis is very long.

The above dynamic electrochemical analysis problems can be very severe when the specific ion sensor suffers from capacitive or any energy storage characteristics in the electrolytic solution. The capacitance function in a dynamic electrochemical analysis requires that the specific ions must either enter or leave the region of the sensor for the voltage output to change. In the optimum form of the coulometric titrator, the transfer of the specific ions and voltage output change are usually independent of the specific ion concentration in the solution and dependent only on the physical construction of the sensor. However, where the capacitance function is encountered, these relationships are no longer valid and appreciable time delay errors arise in this electrochemical analysis.

Unfortunately, the capacitive function about the sensor electrode produces a time delay that becomes proportionally larger as the concentration of the specific ions approaches equivalence. At equivalence concentration levels of the specific ions, the time delay problem causes the most error in the electrochemical analysis since the sensor fails to indicate by output voltage the endpoint until some extended period of time after the actual endpoint has been passed by the continued addition of the reactive ion.

The novel coulometric titrator of this invention is arranged to avoid the problems of the time delay error and capacitance function about the sensor electrode. In this coulometric titrator, the new and novel improvement in electrochemical analysis is achieved by scaler (non-time domain) circuitry which reduces the rate of reactive ion addition logarithmically throughout the analysis. In the preferred embodiment of the coulometric titrator, the addition of the reactive ion is made proportional to the ratio of the antilogarithm of the specific ion sensor's voltage output and a certain rate controlling reference voltage. In this coulometric titrator, the factor change in the specific ion concentration remains constant and yields a linear rate of sensor voltage change with time. As a result, any dynamic time delay arising from the characteristics of the sensor in detection specific ion concentration will have a rate controlling influence and not an endpoint controlling influence. The linear rate of change of sensor output voltage with time is set by the rate controlling reference voltage. Thus, the coulometric titrator of the present invention provides not only high speed titrations of great accuracy, but it employs the linear sensor output voltage change to indicate to the operator that the choice of electrochemical analysis parameters is correct.

Since this titrator has been designed to provide reactive ion proportional to the amount of specific ion left to titrate and has no capability for any other reactive ion demand, the stopping point occurs when some unexpected reactive ion demand becomes the predominant user of the available reactive ion. This unexpected reactive ion demand is usually the demand for storage of the reactive ion in solution as free ion. Because the characteristics of ions in solution determine the stopping point, any zero shift in sensor voltage does not change the stopping point, but only changes the rate of speed that the stopping point is approaching. The new and novel design thus permits accurate operation and accurate answers even though the sensor voltage signal has unexpectedly or even intensionally been shifted by some d.c. amount. Other titrators are very dependent on the use of a stable sensor voltage signal and any unexpected shift in sensor voltage signal will cause considerable error in the answer without the operator being conscious of the problem.

SUMMARY OF THE INVENTION

In accordance with this invention, there is provided a coulometric titrator for determining the amount of a specific ion in a sample electrolytic solution by the controlled addition of a reactive ion. This titrator includes a reference electrode providing a first signal voltage and a specific ion sensing electrode providing a second signal voltage representing the logarithm of the concentration of the specific ion in the same solution which these electrodes are immersed. A differential input amplifier receives these first and second signal voltages as its input and provides in its output an error signal voltage representing the difference between the first and second signal voltages. A reference means provides reference voltage for the specific ion in the solution indicative of a particular rate of change of the second signal voltage while the rate of change of the second signal voltage is constant. Comparator means receive the error signal and the referenced voltage as inputs and has an output of a sensor signal voltage representing the difference between the error signal and reference voltage. The sensor signal voltage is applied to an antilogarithm converter means which produces an output signal that is proportional to the antilogarithm of the sensor signal voltage. Reactive ion source means receive the output signal and are associated with a current source providing a unidirectional current flow between a cathode and an anode immersed in the same solution (one being inert and the other being the reactive ion means) such that the quantum rate of the reactive ion introduced into the sample solution is proportional to the control signal. As a result, the second signal voltage changes at a constant rate with time and the reactive ion addition changes in a logarithmically decreasing amount with time in the same solution.

In other embodiments of the invention, a differentiator means may be employed to receive the error signal voltage and to provide a readout representing the change in the error signal voltage with time. When the proper rate controlling reference voltage has been selected, this readout is a steady state signal of between 10 and 60 millivolts per minute. A coulometric means may be employed to monitor the coulombs supplied to the reactive ions source means.

DESCRIPTION OF SPECIFIC EMBODIMENTS

Figure 1:
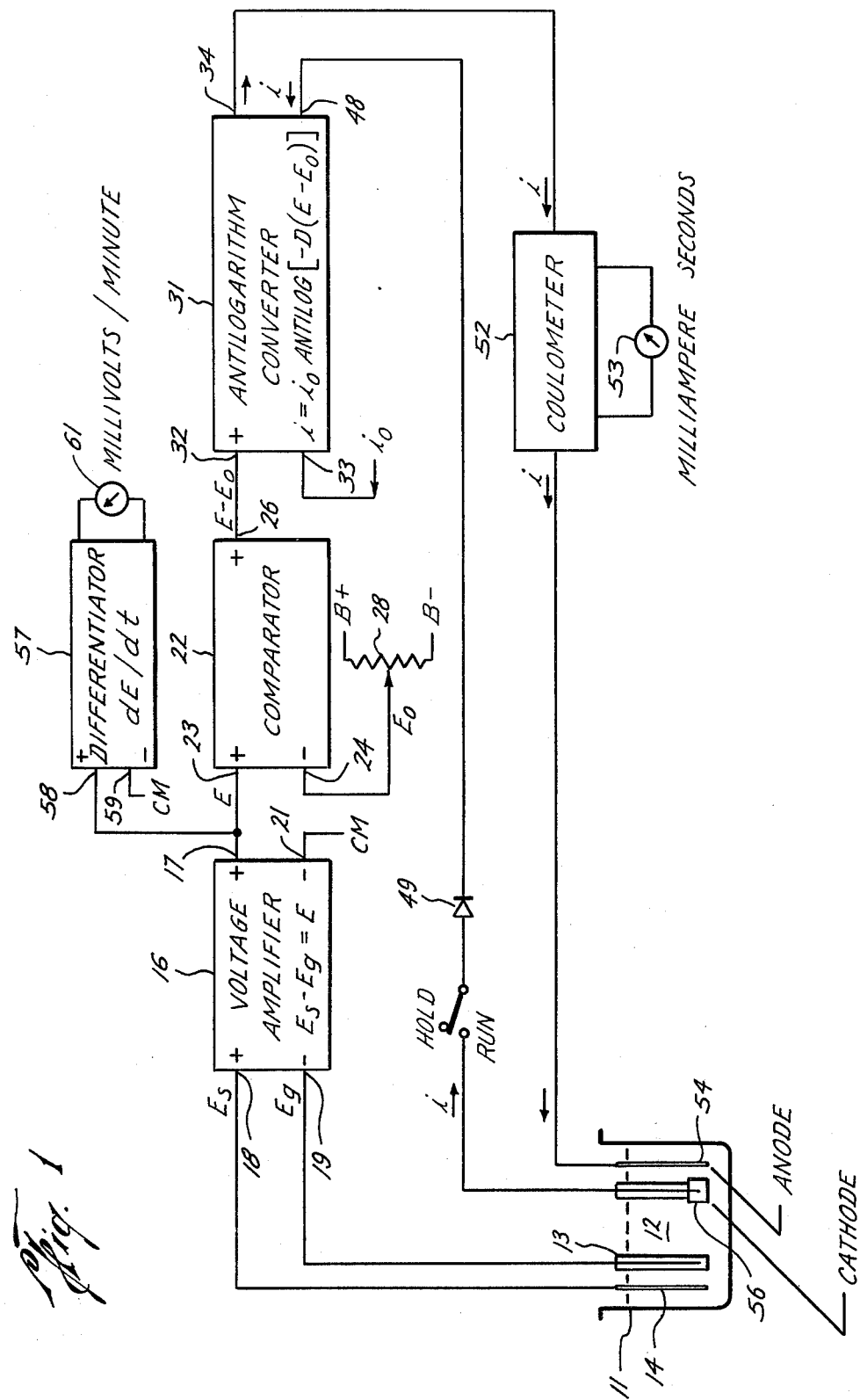
FIG. 1 is an electrical block diagram showing the various elements comprising the coulometric titrator of this invention.

In FIG. 1, there is shown a preferred embodiment of the coulometric titrator of the present invention. The coulometric titrator, as identified by legends, has a plurality of electrical circuit components contained within the various blocks, all components being available in the marketplace or known to the skilled electrochemical analyzer manufacturer. More particularly, the coulometric titrator employs a cell 11 containing the electrolytic solution incorporating the specific ion to be subjected to electrochemical analysis. The solution 12 is of any suitable volume and preferably is maintained at near ambient or other steady state temperature. Immersed within the solution 12 are a plurality of electrodes associated with the coulometric titrator. These electrodes include a reference electrode 13 to produce a first signal voltage $E_g$, and can be a glass electrode for present descriptive purposes. Closely associated with the reference electrode 13 is a specific ion sensing electrode 14 to produce a second signal voltage $E_s$ representing the logarithm of the amount of the specific ion in the sample solution 12. For example, the specific ion may be the chloride ion and the electrode 14 can be a silver/silver chloride half cell embodiment which results in a second signal voltage $E_s$ representing the logarithm of the chloride ion concentration in the solution 12.

The voltages $E_g$ and $E_s$ are applied to a differential amplifier 16 which is arranged to produce in its output 17 an error signal voltage ($E_s - E_g = E$) representing the difference between the first and second signal voltages obtained from the cell 11. The amplifier 16 may be a conventional type having high input impedance and high common mode rejection. Preferably, the amplifier 16 is an amplifier with dual inputs and outputs having positive and negative inputs 18 and 19 receiving the first and second signal voltages $E_g$ and $E_s$, respectively. The amplifier 16 has positive output 17 and negative output 21 providing the error signal voltage E. The amplifier 16 can have a component gain of 40,000 or greater, but preferably the components of the circuit associated with this amplifier adjust the input-output circuit gain to approximately unity. This gain arrangment of the amplifier 16 with input circuitry has an exceedinly high loop impedance, stability and a high common mode of rejection. The amplifier 16 has the usual connections for receiving power and circuit common (CM) which connections have been omitted for simplifying the present description.

The output E of the amplifier 16 is applied to a comparator 22 which is arranged to compare error signal voltage E at a positive input 23 with a rate controlling voltage $E_o$ at a negative input 24 and produce a sensor signal voltage $E - E_o$ at a positive output 26. The rate controlling voltage $E_o$ may be taken from a power source represented by terminal B+ and B− through a variable resistor 28. The rate controlling voltage $E_o$ is obtained through adjustment of the resistance 28 so that a certain voltage magnitude is applied to the input 24 of the comparator 22. The forthcoming description will make clear how this certain value of the reference voltage is selected. This certain magnitude of rate controlling voltage produces the desired endpoint for electrochemical analysis and proper operation of the present coulometric titrator.

The comparator 22 can be of any circuitry performing the defined function $E - E_o$ and amplifiers with dual inputs-outputs arrangement adjusted for unity circuit gain can be employed to good result. The comparator 22 has the usual connections to a source of power and circuit common (CM) which are omitted for simplicity of description. The output 26 of the comparator 22 carries the sensor signal voltage $E - E_o$ to an antilogarithm converter 31.

The antilogarithm converter 31 receives the sensor signal voltage $E - E_o$ and a referencing current $i_o$ and performs the function of producing a control signal $i$ which is proportional to the antilogarithm of the sensor signal voltage $E - E_o$.

The antilogarithm converter 31 is preferably an operational amplifier particularly arranged by circuit components in an antilogarithmic function amplifier. The amplifier employs a semiconductor junction which produces an exponential current-voltage relationship. Although there are a number of commercial devices suitable for employment as the antilogarithm converter 31, it is preferred to employ the IC module available commercially as the Intersil 8049 which may be purchased from Intersil, Inc.

The antilogarithm converter 31 receives the sensor signal voltage $E - E_o$ at an input 32 and a referencing current $i_o$ at its other input 33, which current sets the dynamic range in the operation of the antilogarithm conversion. The antilogarithm converter 31 functions to produce an output signal (current) $i$ that is proportional to the antilogarithm of the sensor signal voltage E. The output 34 of the antilogarithm converter 31 is a current $i$ applied to the cell 11.

The output signal current $i$ has a magnitude which is coulometrically proportional to the rate of addition of the reactive ion into the sample solution. The current flow from the output 34 of the antilogarithm converter 31 is passed into the cell 11 through any suitable means for monitoring the total accumulation of current. Preferably, a coulometer 52 is inserted between the output 34 of the antilogarithm converter 31 and a source of reactive ions contained in the cell 11. The coulometer 52 can be of conventional form and provides a readout indicating the total coulombs which have been passed into the cell 11. This readout may be displayed upon suitable meter 53 calibrated in current-time increments such as milliampere seconds.

The output signal current $i$ from the coulometer 52 passes to a reactive ion source 54 contained in the cell 11 which may be either the anode or cathode. The reactive ion source is usually a metal from which current flow releases metal ions into the solution 12. For example, in a choride ion analysis the reactive ion is the silver ion introduced into the solution 12. Thus, the reactive ion source 54 will be the anode and is a relatively pure electrode formed of metallic silver. The flow of the output signal current $i$ from the antilogarithm converter 31 produces quantitatively the introduction of the reactive ion into the solution 12 in accordance with Faraday's Law. As a result, sensor signal voltage $E - E_o$ applied to the antilogarithm converter 31 results directly in output signal current flow $i$ for the quantitative rate of introduction of the reactive ion into the solution 12. The current $i$ returns from the solution 12 through the cathode formed by an inert electrode 56 to output 48 of the antilogarithm converter 31. The inert electrode 56 forms the cathode for the cell 11 and the reactive ion source 54 serves as the anode for the current flow $i$ from the antilogarithm converter 31 in this example. In other instances, the anode can be inert and the cathode forms the reactive ions source.

Figure 2:
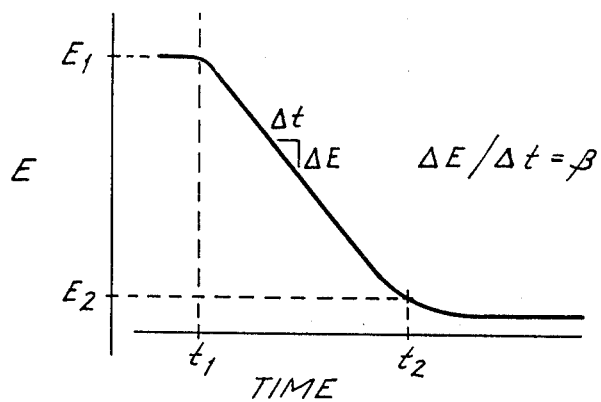
FIG. 2 is a graph illustrating the linear sensor signal voltage change with time to the comparator means for a properly selected reference voltage.
Figure 3:
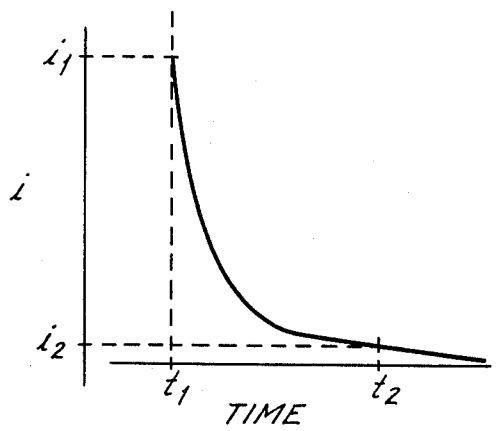
FIG. 3 is a graph illustrating the current flow to the reactive ion source means with the proper reference voltage making the sensor signal voltage change with time in a linear relationship.

The magnitude of the rate control voltage $E_o$ applied at input 24 to the comparator 22 is adjusted in the following manner. The sensor signal voltage $E - E_o$ provided in the output 26 of the comparator 22 reflects the proper adjustment of the rate control voltage $E_o$ when $E - E_o$ changes at an intial constant rate with time between $E_1$ and $E_2$ representing the endpoint. Stated in another manner, as the sensor signal voltage $E_s$ changes with time, it will have an initial constant slope $\Delta E$ between $E_1$ and $E_2$ which may be visualized in reference to FIG. 2. Assume that the sensor signal voltage $E_s$ begins at the error signal $E_1$ and progresses at a uniform rate between times $t_1$ and $t_2$. For a given electrochemical analysis, the rate control voltage $E_o$ will be preset to a certain value, e.g., 1.52 volts, to produce a selected $\Delta E$, e.g., 30 millivolts per minute. This desired constant rate of change of the sensor signal voltage with time can be detected by employing a differentiator 57 which has a positive input 58 connected to the output 17 of the amplifier 16. The negative input 59 of the differentiator 57 is returned to circuit common (CM). The differentiator 57 is a suitable type of operational amplifier which produces an output voltage substantially in proportion to the rate of change of the input voltage with time. The output voltage of the differentiator 57 is displayed on a readout device 61 which may be calibrated in a volt-time function such as millivolts/minute. Using the differentiator 57, the rate control voltage $E_o$ is adjusted by employing the variable resistor 28 until the desired constant rate of change is indicated on the readout device 61 for the certain rate control voltage $E_o$. It has been found with practical embodiments of the present coulometric titrator that the sensor signal voltage $E - E_o$ will change with time between 10 and 60 millivolts per minute for most electrochemical analysis. However, good results have been obtained with the sensor signal voltage $E - E_o$ changing with time at a rate of about thirty millivolts per minute. This rate of thirty millivolts/minute is especially useful where the coulometric titrator is determining the amount of chloride ion within the solution 12 using a silver metal electrode as the reactive ion source 54.

The reactive ion is thus introduced into solution at a rate which is proportional to the demand for the reactive ion. While the demand for the reactive ion is predominately from the specific ion (chloride) at some distance from the stoichiometric endpoint, the resulting rate of change of sensor voltage will be constant. Near the stoichiometric endpoint, the demand for free silver in solution starts to manifest itself. At the stoichiometric endpoint, the demand by the chloride and the demand for free silver becomes equal resulting in a sensor electrode voltage rate of change of one-half. Once past the endpoint, the free silver demand becomes so large with respect to available silver addition that the sensor electrode rate of change will have dropped to a tenth with only a 28 millivolt movement past the endpoint and the titration for all practical purposes will have been stopped.

Because the instrument has been designed to track only the demand for silver by the chloride ion, the titration comes to a halt a small distance past the endpoint because the demand for free silver in solution becomes predominate and soaks up what little silver generating capability is left and the titration of chloride has stopped. A coulometer in the silver generating loop records the number of coulombs that has passed which is a direct measure of the amount of chloride that has been titrated.

It is important to note that changing the reference voltage mentioned earlier will change the rate of change of the sensor voltage but will not change the coulometer reading. This relatively insensitive response to the reference voltage or any other shift in sensor voltage allows this instrumental technique to stand aside from all other known instrumental techniques.

SPECIFIC EXAMPLE

In one specific application of the coulometric titrator heretofore described, the electrochemical analysis of the solution 12 for chloride ion has found to be excellent in operation accuracy. For this purpose, the specific ion sensing electrode 14 is a silver/silver chloride electrode, and the reactive ion source 54 is a relatively pure silver metal electrode. The output voltage $E_s$ of the sensor electrode 14 changes logarithmically relative to the concentration of the chloride ion and is compared voltagewise in amplifier 16 to the relatively constant voltage $E_g$ of the reference electrode 13. The amplifier 16 provides an output error signal E representing the arithmetic summation of these two voltages $E_g$ and $E_s$; comparator 22 combines the error signal E with the reference voltage $E_o$ (sum or difference) to provide the sensor signal voltage $E - E_o$. With the reference voltage $E_o$ set to the proper magnitude as has been explained, the control signal $E - E_o$ applied to the antilogarithm converter 31 produces the proper magnitude of output signal current $i$ (in a logarithmically decreasing amount) throughout the analysis procedure until the endpoint (stoichiometric) is approached at which time the current flow substantially terminates. The cell 11 "coasts" to the ultimate endpoint and the quantum of current $i$ is proportional to the chloride ion originally present in the solution 12.

The present circuitry of the coulometric titrator does not employ a feedback loop susceptible to delay time errors. The variation in the period between times $t_x$ and $t_2$ have no effect on analysis accuracy since the proper selection of the rate control voltage $E_o$ brings the sensor signal voltage $E - E_o$ to time $t_x$ at a steady rate of change with time. Since the mass transfer delay of diffusion of the reactive ions is relatively constant in the present coulometric titrator, proper selection of the rate control signal voltage $E_o$ for a constant rate of change with time of the sensor signal voltage $E - E_o$ automatically compensates for the "coasting" from time $t_x$ to the proper endpoint at time $t_2$ after the flow of current from the antilogarithm converter 31 has been terminated. This adjustment of the circuitry is easily obtained through the use of differentiator 57 and adjustable rate control voltage $E_o$. The coulometric titrator of the present invention inherently produces the desired electrochemical analysis with high accuracy without over addition of the reactive ion and without complicated adjustments.

The control signal current $i$ is a function of a scaler circuitry in the antilogarithm converter 31. No signal processing is accomplished with time domain circuitry such as voltage sweep generators, integrators, differentiators or other types of amplifiers which have an electrical function variant relative to time intervals. All that is required in the coulometric titrator is to adjust the rate control voltage $E_o$ to the certain magnitude whereat $E_s$ changes linearly with time at the necessary rate, e.g., 30 millivolts per minute.

Figure 4:
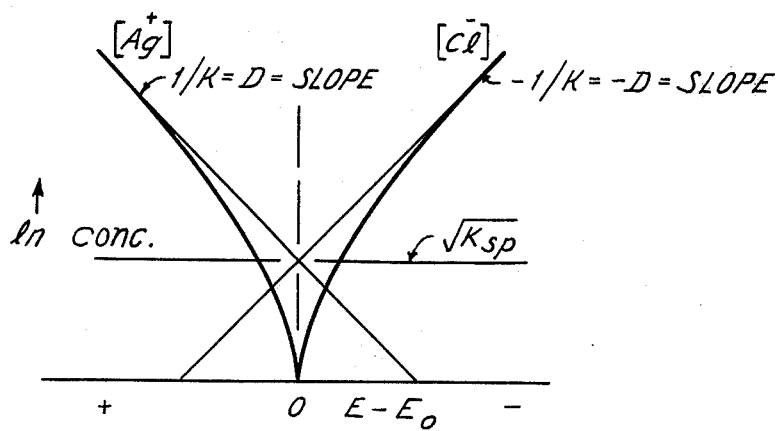
FIG. 4 is a graph illustrating the Tafel slope curves and solubility product, relative to sensor electrode voltages in a sample solution.

The functioning of the present coulometric titrator as to the "Specific Example" can be better understood by reference to FIG. 4 and the following electrochemical equations which define the unique operating parameters. FIG. 4 is a graphic representation of a typical sample solution where the concentration of chloride ions (Cl−) is determined by addition of silver ions (Ag+) until an endpoint (stoichiometric) is reached as represented by the solubility product $K_{sp}$ of silver chloride (AgCl). In FIG. 4, and in the following equations the identification of sensor signal voltage E-$E_o$, error signal voltage E, etc., are retained and are used consistently. The voltage E may be taken as the half cell voltage relative to the sample solution in the graph and as the error signal voltage E from amplifier 16.

Particularly, the concentration of silver ions [Ag+] and chloride ions [Cl−] is given as:

Equation 1: $[Ag^+] = \sqrt{K_{sp}}\, e^{+DE} = Ag/v$, where $v$ = volume of solution, or Equation 2: $AG = v\sqrt{K_{sp}}\, e^{+DE}$ Equation 3: $[Cl^-] = \sqrt{K_{sp}}\, e^{-DE} = Cl/v$, or Equation 4: $Cl = v\sqrt{K_{sp}}\, e^{-DE}$ The total amounts of ions are:

Equation 5: $Ag = Ag_x + Ag_s$

Equation 6: $Cl = Cl_x + Cl_s$

Equation 7: $Ag_s/v = Cl_s/v = S =$ individual ions solubility for all E; therefore, $Ag_x = Cl_x = 0$ at $E = 0$. At the solution parameters, when Equation 8: $Ag_x \neq 0$, $Cl_x = 0$, $E > 0$, $S = [Cl^-] = Cl_s/v = Cl/v$ when Equation 9: $Cl_x \neq 0$, $Ag_x = 0$, $E < 0$, $S = [Ag^+] = Ag_s/v = Ag/v$.

The silver chloride solubility product has the following relationship:

Equation 10:
$$[Ag^+][Cl^-] = K_{sp} = \left(\frac{Ag}{v}\right)\left(\frac{Cl}{v}\right) = \left(\frac{Ag_x + Ag_s}{v}\right)\left(\frac{Cl_x + Cl_s}{v}\right);$$

then For $E > 0$,

Equation 11: $Ag_x = Ag - Ag_s = \nu\sqrt{K_{sp}}(e^{+DE} - e^{-DE}) = \nu\sqrt{K_{sp}}(2 \sinh DE)$ $-Cl_x = 0$; and For $E < 0$, Equation 12: $-Cl_x = -(Cl - Cl_s) = -\nu\sqrt{K_{sp}}(e^{-DE} - e^{+DE}) = \nu\sqrt{K_{sp}}(2 \sinh DE)$ $Ag_x = 0$ Equation 13: $Ag_D =$ silver demand $= \Sigma Q_{Ag}$ Adding positive silver ions decrease negative chloride ions because their reaction product is an insoluble material. Combining equations 11 and 12, For $E > 0$, Equation 14: $Ag_D = Ag_x - Cl_x = \nu\sqrt{K_{sp}}(2 \sinh DE) - 0 = 2\nu\sqrt{K_{sp}} \sinh DE$, or For $E < 0$, Equation 15: $Ag_D = Ag_x - Cl_x = 0 + \nu\sqrt{K_{sp}}(2\sinh DE) = 2\nu\sqrt{K_{sp}} \sinh DE$ From Equations 14 and 15, it is obvious that:
For all $E$, Equation 16: $Ag_D = 2\nu\sqrt{K_{sp}} \sinh DE$, and Equation 17: $dAg_D/dt = 2\nu\sqrt{K_{sp}}(d(DE)/dt) \cosh DE$, or Equation 18: $dAg_D/dt = 2\nu D\sqrt{K_{sp}} dE/dt \cosh DE$ at the silver generator anode, the output signal current resolves to:

Equation 19:

$$\frac{dQ_g}{dt} = i = -F\frac{dAg_i}{dt} = -F\frac{dAg_D}{dt};$$

since $\dfrac{dAg_D}{dt} = \dfrac{dAg_i}{dt}$ and $\dfrac{dQ_g}{dt} = \dfrac{d(\Sigma Q_{Ag})}{dt}$.

From Equation 19,

Equation 20: $dAg_D/dt = -i/F$; and

From Equation 18 and 20,

Equation 21: $dAg_D/dt = -i/F = 2\nu D\sqrt{K_{sp}}(dE/dt) \cosh DE$; and from Equation 21, Equation 22: $dE/dt = -i/2F\nu D\sqrt{K_{sp}} \cosh DE$ If $dE/dt =$ constant $= \beta$, then $-i = \beta(2F\nu D\sqrt{K_{sp}}) \cosh DE$; or, Equation 23: $-i = \beta(F\nu D\sqrt{K_{sp}})(e^{+DE} + e^{-DE})$ or, Equation 24: $-i = \beta(F\nu D\sqrt{K_{sp}})(\text{antilog}(+DE) + \text{antilog}(-DE))$ A coulometric titrator can be built to satisfy equation 24 using two antilog converters, whose outputs are added to each other to control a proportional generator current in the sample cell 11. However, the sensor signal $E - E_o$ must be inverted to one of the antilog converters. The biggest problem with this arrangement is the corrected sensor voltage must be proportional to DE and must be zero at the equivalence point. If $K_{sp}$ changes, E has a zero shift or the cell temperature changes the rate of sensor voltage change $dE/dt$ will not be constant. This arrangement requires too much knowledge about the sample cell and unknown sample solution to be practical in nonaqueous solutions wherein the $K_{sp}$ of silver chloride is small but very changeable as the amount of water changes in the cell. A change in $K_{sp}$ cause the sensor signal voltage $E - E_o$ to have a zero shift.

The coulometric titrator design of the present invention does not require prior knowledge of $K_{sp}(AgCl)$ or location of $E_o$ with respect to the equivalence point! The cell temperature can also change, the valence of the unknown sample can change, and the coulometric titrator can still yield a good (but not as accurate) answer as if they had not changed. This new and novel coulometric titrator design depends on starting and finishing the rates of change of sensor signal voltage $E - E_o$ and not on the actual value of rate control voltage $E_o$ itself. This new instrument design cannot be "fooled" by inserting an unknown series voltage in series with the signal voltage $E_s$.

This new coulometric titrator uses only one antilog converter 31 rather than the two necessary for $dE/dt =$ constant for all magnitudes of E. However, $dE/dt =$ constant is for concentrations of unknown ions that are much larger than existed at the equivalence point. Nonaqueous solutions in the cell 11 make the solubility product of the unknown ion ($Cl^-$) and silver ($Ag^+$) very much smaller in magnitude, and therefore, the starting $dE/dt$ is constant for most of the unknown samples. Under these circumstances and from equation 24, the antilog converter 31 only has to follow the chloride characteristics since by instrument design, Equation 25: Antilog $(+DE) = 0$, because this converter is omitted, Therefore, from Equations 24 and 25, Equation 26: $-i + \beta(F\nu D\sqrt{K_{sp}})(0 +$ antilog $(-DE)$. By instrument design, Equation 27: $-i + \beta(+F\nu D\sqrt{K_{sp}})$ antilog $(-DE)$. By instrument design, Equation 28: $K_c + \beta(+F\nu D\sqrt{K_{sp}}) =$ antilog converter constant.

With the antilog converter 31, $K_c$ can be changed by changing the converter reference current, $i_o$, and/or by adding or subtracting a biasing voltage to its input voltage $E - E_o$. Now Equation 27 becomes Equation 29: $i = i_o$ antilog $\{-D(E-E_o)\}$ Equation 30: $i = i_o(\text{antilog}(-DE + DE_o)) = i_o e^{+\lambda} DE_o \text{antilog}(-DE) = K_c \text{antilog}(-DE)$.

From equation 30,

Equation 31: $K_c = i_o e^{+DE_o}$

Combining Equation 28 and 31,

Equation 32: $K_c = i_o e^{+DE_o} = \beta(+F\nu D\sqrt{K_{sp}}) = (+\beta F\nu)(D\sqrt{K_{sp}})$; and Equation 33: $K_c = (+\beta F\nu)e^{+D(1/D \ln D^\circ D_{sp})} = i_o e^{+DE_o}$ From Equation 33, substitute:

$i_o = +K_1 F\nu$ $$E_o = (1/D)\ln D\sqrt{K_{sp}} = 1/(D \ln D\sqrt{K_{sp}})$$

$$\beta = +dE/dt \text{ at start while } (E - E_o) << 0.$$

Combining Equations 27 and 22,

Equation 34:

$$\frac{dE}{dt} = \frac{\beta(+FvD\sqrt{K_{sp}})\text{antilog }(-DE)}{2FvD\sqrt{K_{sp}}\cosh DE} = \frac{+\beta e^{-DE}}{2\cosh DE} \text{; or}$$

Equation 35:

$$\frac{dE}{dt} = \frac{\beta e^{-DE}}{e^{+DE} + e^{-DE}} \text{ and}$$

Equation 36:

$$\frac{dE}{dt} = +\beta\left(\frac{1}{e^{+2DE} + 1}\right).$$

In the case, $E << 0$, then

Equation 37: $dE/dt = +\beta(1/0+1) = +\beta$

In the case, $E >> 0$, then

Equation 38:

$$\frac{dE}{dt} = +\beta\left(\frac{1}{e^{+2\Delta E} + (\approx 0)}\right) = +\beta e^{-2DE}$$

As a result, for $E >> 0$,

Equation 39: $dE/dt = +\beta E^{-DE}$

In the case, $E = 0$, then

Equation 40: $dE/dt = +\beta(1/(1 + 1)) = \frac{1}{2}(+\beta)$ let $\alpha$ = sensor voltage $E - E_o$ rate reduction factor = $\dfrac{\beta}{\dfrac{dE}{dt}}$ and determined by the rate control voltage $E_o$. Therefore, Equation 41:

$$\alpha = \frac{\beta}{\frac{dE}{dt}} = \beta \frac{dt}{dE}$$

The present coulometric titrator is applicable to various studies in electrochemical analysis, and it is not limited merely to the described potentiometric precipitation titration embodiment of the chloride ion determination in solution 12 by its reaction with coulometrically introduced silver ions. Other uses for the coulometric titrator include: potentiometric oxidation-reduction titrations, determination of ionization constant and solubility product constant, and coulometric electrolysis wherein the working electrode potential control will be automatically obtained.

Various modifications and alterations which do not depart from the spirit of the invention in the described coulometric titrator will be apparent to those skilled in the art from the foregoing description. For this reason, these changes in elements and functioning are desired to be included within the scope of the present invention. The appended claims define the present invention and the foregoing description is to be employed for setting forth these specific embodiments as illustrative in nature.

What is claimed is:

1. A coulometric titrator for determining the amount of a specific ion in a sample solution by the reaction with a reactive ion comprising:
   a. a cell for containing said sample solution and including electrodes for immersion in said solution, said electrodes including a reference electrode providing a first signal voltage and a specific ion sensing electrode providing a second signal voltage representing the logarithm of the concentration of the specific ion in said sample solution;
   b. differential input amplifier means having as inputs said first and second signal voltages from said reference and specific ion sensing electrodes and said differential input amplifier having as its output an error signal voltage representing the difference between said first and second signal voltages;
   c. reference means providing a reference voltage for the specific ion in the solution indicative of a particular rate of change of the second signal voltage while said rate of change of the second signal voltage is constant;
   d. comparator means receiving as inputs said error signal voltage and said reference voltage and providing as its output a sensor signal voltage representing the difference between said error signal and reference voltages;
   e. antilogarithm converter means receiving said sensor signal voltage and having an output signal that is proportional to the antilogarithm of said sensor signal voltage; and
   f. reactive ion source means in the sample solution receiving said output signal and associated with a current source providing an unidirectional current flow between an anode and a cathode immersed in the sample solution and said reactive ion source means is either the anode or the cathode with the other being inert and with the quantum rate of reactive ion introduction into the sample solution being proportional to said output signal, whereby said second signal voltage changes at a constant rate with time and said reactive ion addition changes in a logarithmically decreasing amount with time in the sample solution until the stoichiometric endpoint is approached.

2. The coulometric titration of claim 1 wherein a differentiator means receives as its input said error signal voltage and provides as an output a readout signal representing the change in the second signal voltage with time.

3. The coulometric titrator of claim 2 wherein said readout signal represents a change in sensor signal voltage with time between 10 and 60 millivolts per minute.

4. The coulometric titrator of claim 1 wherein a coulometer means monitors said current flow from said current source and provides a readout of the total coulomb amount.

5. The coulometric titrator of claim 1 wherein said specific ion sensing electrode is adapted for sensing chloride ions and said reactive ion source means is a silver metal electrode.

6. The coulometric titrator of claim 1 wherein said reactive ion source means is the anode.

* * * * *